United States Patent
Lalena et al.

(10) Patent No.: US 8,821,017 B2
(45) Date of Patent: Sep. 2, 2014

(54) PROJECTOR AS COLLIMATOR LIGHT

(75) Inventors: Michael C. Lalena, Webster, NY (US); Xiaohui Wang, Pittsford, NY (US); Joseph E. Stagnitto, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 253 days.

(21) Appl. No.: 13/284,218

(22) Filed: Oct. 28, 2011

(65) Prior Publication Data

US 2012/0039447 A1 Feb. 16, 2012

Related U.S. Application Data

(63) Continuation-in-part of application No. 13/083,860, filed on Apr. 11, 2011.

(60) Provisional application No. 61/323,476, filed on Apr. 13, 2010, provisional application No. 61/449,932, filed on Mar. 7, 2011.

(51) Int. Cl.
*A61B 6/08* (2006.01)
*A61B 6/00* (2006.01)

(52) U.S. Cl.
CPC . *A61B 6/08* (2013.01); *A61B 6/542* (2013.01); *A61B 6/4266* (2013.01); *A61B 6/4291* (2013.01); *A61B 6/4405* (2013.01); *A61B 6/4108* (2013.01)
USPC .......................................... 378/206; 378/98

(58) Field of Classification Search
USPC .......................................... 378/205–206, 90
See application file for complete search history.

(56) References Cited

U.S. PATENT DOCUMENTS

| | | | |
|---|---|---|---|
| 4,017,858 A | 4/1977 | Kuipers |
| 4,246,486 A | 1/1981 | Madsen |
| 4,752,948 A | 6/1988 | MacMahon |
| 4,836,671 A | 6/1989 | Bautista |
| 5,241,578 A | 8/1993 | MacMahon |
| 5,388,143 A | 2/1995 | MacMahon |
| 5,539,798 A | 7/1996 | Asahina et al. |
| 5,550,889 A | 8/1996 | Gard et al. |
| 5,617,462 A | 4/1997 | Spratt |
| 5,751,783 A | 5/1998 | Granfors et al. |
| 5,949,811 A | 9/1999 | Baba et al. |
| 6,047,042 A | 4/2000 | Khutoryansky et al. |
| 6,154,522 A | 11/2000 | Cumings |
| 6,192,105 B1 | 2/2001 | Hunter et al. |

(Continued)

FOREIGN PATENT DOCUMENTS

JP 2000-023955 1/2000

OTHER PUBLICATIONS

International Search Report, International application No. PCT/US2012/0262212, dated Aug. 30, 2012, 2 pages.

(Continued)

*Primary Examiner* — Hoon Song

(57) ABSTRACT

A radiography system for obtaining a radiographic image of a subject, has a radiation source within an enclosure, the radiation source energizable to direct radiant energy along a radiation path toward an imaging receiver, wherein the radiation path is defined according to a collimator. A digital projector is coupled to the enclosure and is energizable to provide an illumination beam that outlines the defined radiation path.

21 Claims, 23 Drawing Sheets

(56) References Cited

U.S. PATENT DOCUMENTS

| | | | |
|---|---|---|---|
| 6,208,710 B1 | 3/2001 | Nagai | |
| 6,327,336 B1 | 12/2001 | Gingold et al. | |
| 6,404,851 B1 | 6/2002 | Possin et al. | |
| 6,422,750 B1 | 7/2002 | Kwasnick et al. | |
| 6,702,459 B2 | 3/2004 | Barnes et al. | |
| 6,760,405 B2 | 7/2004 | Ruetten et al. | |
| 6,895,268 B1 | 5/2005 | Rahn et al. | |
| 6,942,385 B2 | 9/2005 | Fadler et al. | |
| 6,944,266 B2 | 9/2005 | Yamazaki et al. | |
| 6,950,492 B2 | 9/2005 | Besson | |
| 7,010,091 B2 | 3/2006 | Hayashida et al. | |
| 7,120,229 B2 | 10/2006 | Takasawa | |
| 7,156,553 B2 | 1/2007 | Tanaka et al. | |
| 7,345,274 B2 | 3/2008 | Nilsson | |
| 7,368,724 B2 | 5/2008 | Morii et al. | |
| 7,490,986 B2 | 2/2009 | Takekoshi et al. | |
| 7,519,155 B2 | 4/2009 | Mollus et al. | |
| 7,581,884 B1 | 9/2009 | Barnes et al. | |
| 7,601,961 B2 | 10/2009 | Franklin et al. | |
| 7,613,276 B2 | 11/2009 | Sendai | |
| 7,632,016 B1 | 12/2009 | Huang et al. | |
| 7,744,279 B2 | 6/2010 | Health et al. | |
| 7,780,350 B2 | 8/2010 | Tranchant et al. | |
| 7,794,144 B2 | 9/2010 | Windt | |
| 7,798,710 B1 | 9/2010 | Barnes et al. | |
| 2002/0150215 A1 | 10/2002 | Barnes et al. | |
| 2002/0188194 A1 | 12/2002 | Cosman | |
| 2003/0165216 A1 | 9/2003 | Walker et al. | |
| 2004/0101100 A1 | 5/2004 | Morii et al. | |
| 2004/0105526 A1 | 6/2004 | Zhang et al. | |
| 2005/0058244 A1 | 3/2005 | Tanaka et al. | |
| 2005/0169425 A1 | 8/2005 | Takasawa | |
| 2006/0109958 A1 | 5/2006 | Ertel et al. | |
| 2006/0269114 A1 | 11/2006 | Metz | |
| 2007/0030957 A1 | 2/2007 | Pommi | |
| 2007/0244388 A1 | 10/2007 | Sato et al. | |
| 2007/0255087 A1 | 11/2007 | Minai | |
| 2007/0297569 A1 | 12/2007 | Saunders | |
| 2008/0130837 A1 | 6/2008 | Heath et al. | |
| 2008/0198968 A1* | 8/2008 | Takekoshi et al. | 378/62 |
| 2008/0204012 A1 | 8/2008 | Krueger et al. | |
| 2008/0240346 A1 | 10/2008 | Kashiwagi et al. | |
| 2009/0060145 A1 | 3/2009 | Tranchant et al. | |
| 2009/0086926 A1 | 4/2009 | Wang et al. | |
| 2009/0136000 A1 | 5/2009 | Nishii et al. | |
| 2009/0180590 A1 | 7/2009 | Borgmann et al. | |
| 2009/0257561 A1 | 10/2009 | Okuno et al. | |
| 2010/0002831 A1 | 1/2010 | Maack | |

OTHER PUBLICATIONS

Brochure for EasyPos dental x-ray positioning system from website, Mar. 2010, 010.hyphendev.fi file PubEasypos08v3.pdf, 2 pages.
International Search Report & Written Opinion, International application No. PCT/US2011/032020, date Nov. 22, 2011, 8 pages.
International Search Report & Written Opinion, International application No. PCT/US2011/032035, dated Dec. 19, 2011, 9 pages.
Supplementary European Search Report completed Mar. 5, 2014 for European Patent Application No. 11 76 9395.2, 2 pages.
Supplementary Partial European Search Report completed Apr. 29, 2014 for European Patent Application No. 11 76 9406, 1 page.

* cited by examiner

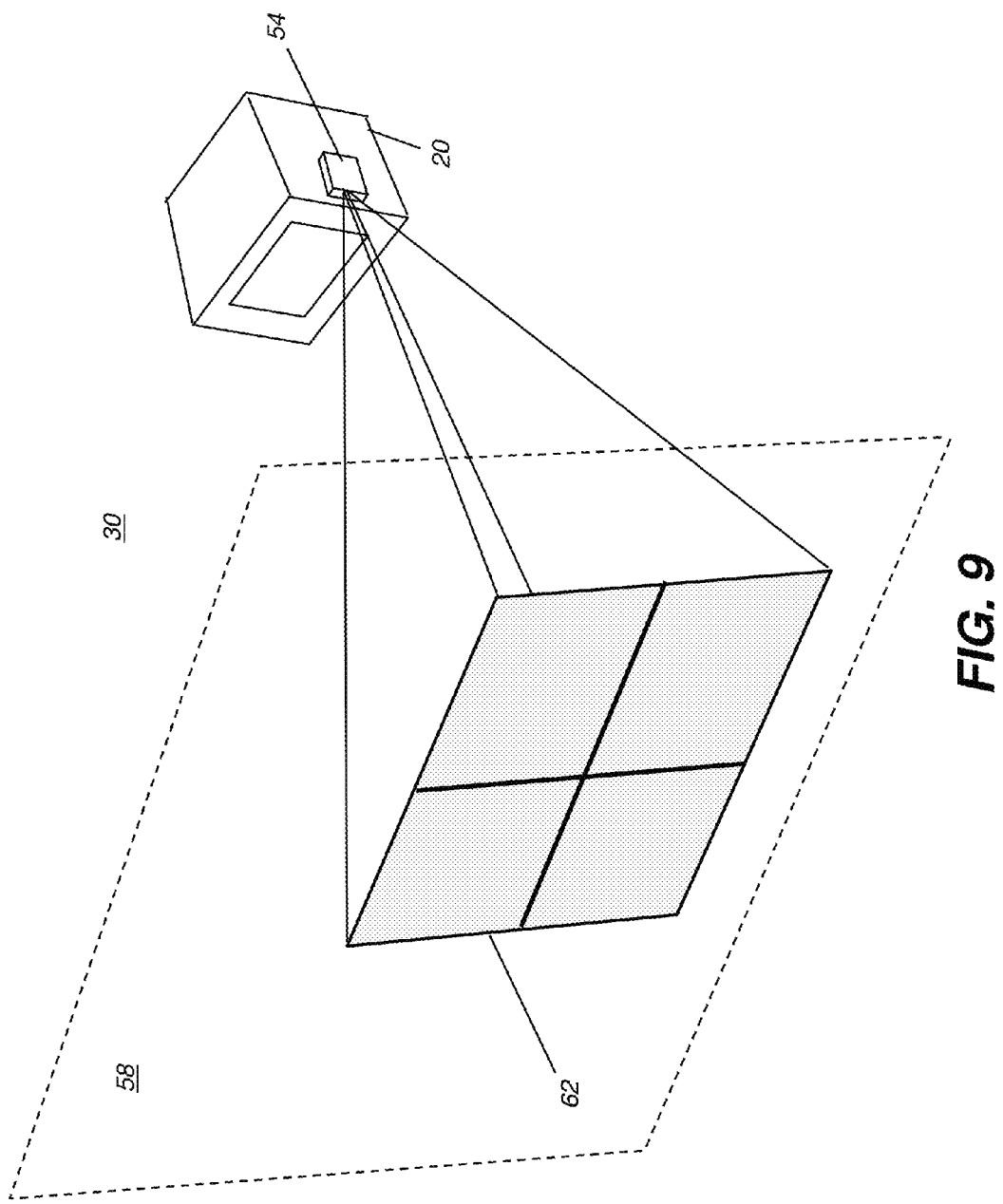

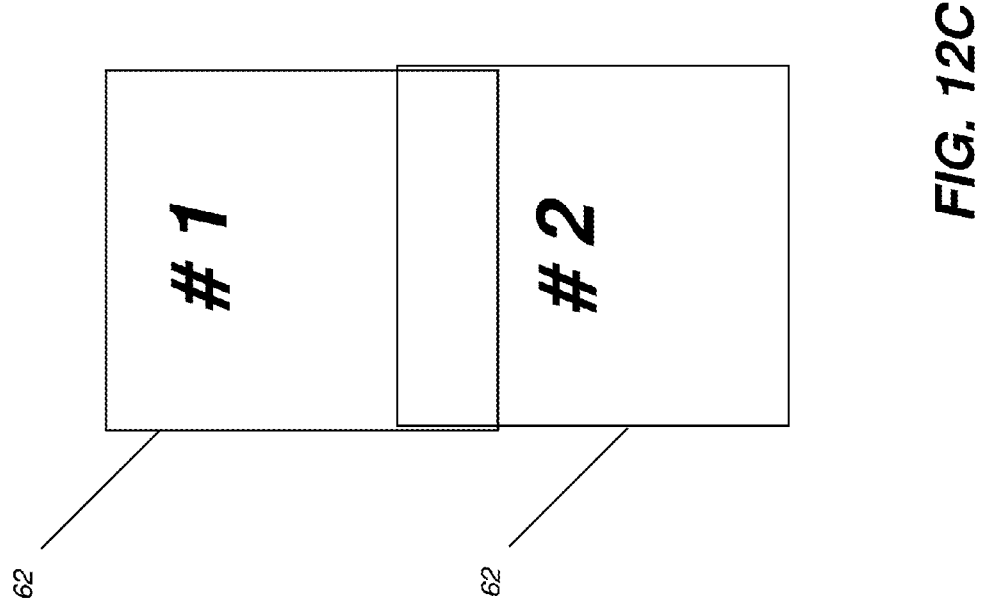

PROJECTOR AS COLLIMATOR LIGHT

CROSS REFERENCE TO RELATED APPLICATION

The present application is a Continuation-in-Part of U.S. Ser. No. 13/083,860 filed Apr. 11 2011 and entitled "TUBE ALIGNMENT FOR MOBILE RADIOGRAPHY SYSTEM" by Lalena et al., which, in turn, claims benefit of U.S. Provisional Application Ser. No. 61/323,476, filed 13 Apr. 2010, entitled "MOBILE UNIT HAVING TUBE ALIGNMENT SYSTEM," by Lalena.

The present application further claims priority to U.S. Provisional Application Ser. No. 61/449,932, filed 7 Mar. 2011, entitled "GRAPHIC USER INTERFACE FOR MOBILE UNIT" by Stagnitto et al.

FIELD OF THE INVENTION

The invention relates generally to the field of radiographic imaging, and in particular to alignment apparatus for the x-ray source in a radiographic imaging system. More specifically, the invention relates to an apparatus and method for using a projector as an indicator of the area that lies in the path of the exposure beam.

BACKGROUND OF THE INVENTION

When an x-ray image is obtained, there is generally an optimal distance and angle between the radiation source and the two dimensional receiver that records the image data. In most cases, it is preferred that the x-ray source provide radiation in a direction that is perpendicular to the surface of the recording medium. For this reason, large-scale radiography systems mount the radiation head and the recording medium holder at a specific angle relative to each other. Orienting the head and the receiver typically requires a mounting arm of substantial size, extending outward well beyond the full distance between these two components. With such large-scale systems, source-to-image distance (SID) is tightly controlled and unwanted tilt or skew of the receiver is thus prevented by the hardware of the imaging system itself. Further, because the spatial positioning and geometry of conventional large-scale systems is well-controlled, proper use and alignment of a grid, positioned in front of the imaging receiver, is straightforward.

Mobile x-ray apparatus are of particular value in intensive care unit (ICU) and other environments where timely acquisition of a radiographic image is of particular value. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

The perspective view of FIG. 1 shows an example of a conventional mobile x-ray apparatus that can be employed for computed radiography (CR) and/or digital radiography (DR). A mobile radiography unit 600 has a frame 620 that includes a display 610 for display of obtained images and related data and a control panel 612 that allows functions such as storing, transmitting, modifying, and printing of the obtained image.

For mobility, unit 600 has one or more wheels 615 and one or more handle grips 625, typically provided at waist-, arm-, or hand-level, that help to guide unit 600 to its intended location. A self-contained battery pack typically provides source power, eliminating the need for operation near a power outlet.

Mounted to frame 620 is a support member 635 that supports an x-ray source 640, also termed an x-ray tube or tube head, mounted on a boom apparatus 170, more simply termed a boom 170. A generator may also be mounted adjacent the tube head or, alternately, within frame 620. In the embodiment shown, support member 635 has a vertical column 64 of fixed height. Boom 170 extends outward a variable distance from support member 635 and rides up and down column 64 to the desired height for obtaining the image. Boom 170 may extend outward by a fixed distance or may be extendible over a variable distance. Height settings for the x-ray source 640 can range from low height for imaging feet and lower extremities to shoulder height and above for imaging the upper body portions of patients in various positions. In other conventional embodiments, the support member for the x-ray source is not a fixed column, but is rather an articulated member that bends at a joint mechanism to allow movement of the x-ray source over a range of vertical and horizontal positions.

With the advent of portable radiation imaging apparatus, such as those used in Intensive Care Unit (ICU) environments, a fixed angular relationship between the radiation source and two-dimensional radiation receiver and any accompanying grid is no longer imposed by the mounting hardware of the system itself. Instead, an operator is required to aim the radiation source toward the receiver surface, providing as perpendicular an orientation as possible, typically using a visual assessment. In computed radiography (CR) systems, the two-dimensional image-sensing device itself is a portable cassette that stores the readable imaging medium. In direct digital radiography (DR) systems, the two-dimensional image-sensing receiver is a digital detector with either flat, rigid, or flexible substrate support.

The receiver itself, however, may not be visible to the technician once it is positioned behind the patient. This complicates the alignment task for portable systems, requiring some method for measuring SID, tilt angle, and centering, and making it more difficult to use a grid effectively for reducing the effects of scatter. Because of this added complexity with a portable radiography system, the technician may choose not to use a grid; the result without a grid, however, is typically a lower-quality image.

There have been a number of approaches to the problem of providing methods and tools to assist operator adjustment of x-ray source-to-receiver angle. One conventional approach has been to provide mechanical alignment in a more compact fashion, such as that described in U.S. Pat. No. 4,752,948 entitled "Mobile Radiography Alignment Device" to MacMahon. A platform is provided with a pivotable standard for maintaining alignment between an imaging cassette and radiation source. However, complex mechanical solutions of this type tend to reduce the overall flexibility and portability of these x-ray systems. Another type of approach, such as that proposed in U.S. Pat. No. 6,422,750 entitled "Digital X-ray Imager Alignment Method" to Kwasnick et al. uses an initial low-exposure pulse for detecting the alignment grid; however, this method would not be suitable for portable imaging conditions where the receiver must be aligned after it is fitted behind the patient.

Other approaches project a light beam from the radiation source to the receiver in order to achieve alignment between the two. Examples of this approach include U.S. Pat. No. 5,388,143 entitled "Alignment Method for Radiography and Radiography Apparatus Incorporating Same" and U.S. Pat.

No. 5,241,578 entitled "Optical Grid Alignment System for Portable Radiography and Portable Radiography Apparatus Incorporating Same", both to MacMahon. Similarly, U.S. Pat. No. 6,154,522 entitled "Method, System and Apparatus for Aiming a Device Emitting Radiant Beam" to Cumings describes the use of a reflected laser beam for alignment of the radiation target. However, the solutions that have been presented using light to align the film or CR cassette or DR receiver are constrained by a number of factors. The '143 and '578 MacMahon disclosures require that a fixed Source-to-Image Distance (SID) be determined beforehand, then apply triangulation with this fixed SID value. Changing the SID requires a number of adjustments to the triangulation settings. This arrangement is less than desirable for portable imaging systems that allow a variable SID. Devices using lasers, such as that described in the '522 Cumings disclosure, in some cases can require much more precision in making adjustments than is necessary.

Other examples in which light is projected from the radiation source onto the receiver are given in U.S. Pat. No. 4,836,671 entitled "Locating Device" to Bautista and U.S. Pat. No. 4,246,486 entitled "X-ray Photography Device" to Madsen. Both the Bautista '671 and Madsen '486 approaches use multiple light sources that are projected from the radiation source and intersect in various ways on the receiver.

Significantly, the solutions noted above are often of little of no value where the receiver and its accompanying grid are hidden from view, lying fully behind the patient as may be the case, for example, for chest x-ray imaging with a portable system. Today's portable radiation imaging devices allow considerable flexibility for placement of the film cassette, CR cassette, or Digital Radiography DR receiver by the radiology technician. The patient need not be in a horizontal position for imaging, but may be at any angle, depending on the type of image that is needed and on the ability to move the patient for the x-ray examination. The technician can manually adjust the position of both the cassette or receiver and the radiation source independently for each imaging session. Thus, it can be appreciated that an alignment apparatus for obtaining the desired angle between the radiation source and the grid and image receiver must be able to adapt to whatever orientation is best suited for obtaining the image. Tilt sensing, as has been conventionally applied and as is used in the device described in U.S. Pat. No. 7,156,553 entitled "Portable Radiation Imaging System and a Radiation Image Detection Device Equipped with an Angular Signal Output Means" to Tanaka et al. and elsewhere, does not provide sufficient information on cassette-to-radiation source orientation, except in the single case where the cassette lies level. More complex position sensing devices can be used, but can be subject to sampling and accumulated rounding errors that can grow worse over time, requiring frequent resynchronization.

Conventional x-ray imaging systems use a collimator to shape the radiation beam, thereby defining the area of the subject that is exposed to x-ray radiation. Typically, the collimator has one or more adjustable flaps or blades that attach to the x-ray head or other source enclosure and are angularly adjustable to define the spread of the x-ray beam. In order to indicate the collimator settings and the shape of the consequent beam path to the x-ray technician during setup, a light bulb, Light-Emitting Diode (LED) or other source of visible light is provided as a collimator light. This collimator light is mounted at a position that is optically equivalent to the position of the x-ray source, so that light that is emitted from the collimator light follows the same path outward from the x-ray head as that of the ionizing radiation that is to be used. Using the collimator light as a guide, the technician can not only change the collimator settings to re-adjust beam path shape, but can also adjust the position or tilt angle of the x-ray head itself, so that the x-ray source is appropriately centered with respect to the subject.

When an x-ray image is obtained, there is generally an optimal distance and angle between the radiation source and the two dimensional receiver that records the image data. In most cases, it is preferred that the x-ray source provide radiation in a direction that is perpendicular to the surface of the recording medium. For this reason, large-scale radiography systems mount the radiation head and the recording medium holder at a specific angle relative to each other. Orienting the head and the receiver typically requires a mounting arm of substantial size, extending outward well beyond the full distance between these two components. With such large-scale systems, source-to-image distance (SID) is tightly controlled and unwanted tilt or skew of the receiver is thus prevented by the hardware of the imaging system itself. Further, because the spatial positioning and geometry of conventional large-scale systems is well-controlled, proper use and alignment of a grid, positioned in front of the imaging receiver, is straightforward.

Mobile x-ray apparatus are of particular value in intensive care unit (ICU) and other environments where timely acquisition of a radiographic image is of particular value. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

For both large-scale and mobile x-ray systems, some type of collimator light is needed in order to guide the operator/technician to making proper collimator adjustments. Once the beam is properly shaped and other variables and parameters appropriately set, the operator/technician can obtain the exposure that is needed.

In addition to accurately knowing the collimator settings, the operator/technician also makes other settings and adjustments for each particular image. With mobile computed radiography (CR) and/or digital radiography (DR) imaging systems, for example, the operator may have a considerable number of added considerations for obtaining the best image in a particular case, including proper power settings, relative positioning of the imaging receiver, use of grids, and positioning of radiation sensing devices that lie in the exposure path and that may be sensed to terminate exposure automatically, for example. The conventional collimator light, however, does not provide information other than to show the relative beam size due to collimator blade settings. Providing more information for the technician or other operator can help to improve workflow efficiency, to reduce excessive exposure or retakes, and to help obtain images under the proper conditions.

SUMMARY OF THE INVENTION

An object of the present invention is to advance the art of radiographic imaging by providing apparatus and methods to aid in alignment and proper positioning of the radiation source relative to a subject. A related object of the present invention is to provide a collimator light that shows the relative size and spread of an x-ray beam that is to be used for imaging and provides additional information that can be used to help improve setup and operation of the x-ray system.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a radiography system for obtaining a radiographic image of a subject, the system comprising: a radiation source within an enclosure, the radiation source energizable to direct radiant energy along a radiation path toward an imaging receiver, wherein the radiation path is defined according to a collimator; and a digital projector that is coupled to the enclosure and is energizable to provide an illumination beam that outlines the defined radiation path.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 9 is a schematic diagram that shows a projected collimator pattern within a larger field that can be used for other projected content.

FIG. 12C is a plan view showing instructional information displayed by a projector when used as collimator light.

DESCRIPTION OF EXEMPLARY EMBODIMENTS

Figure 1:
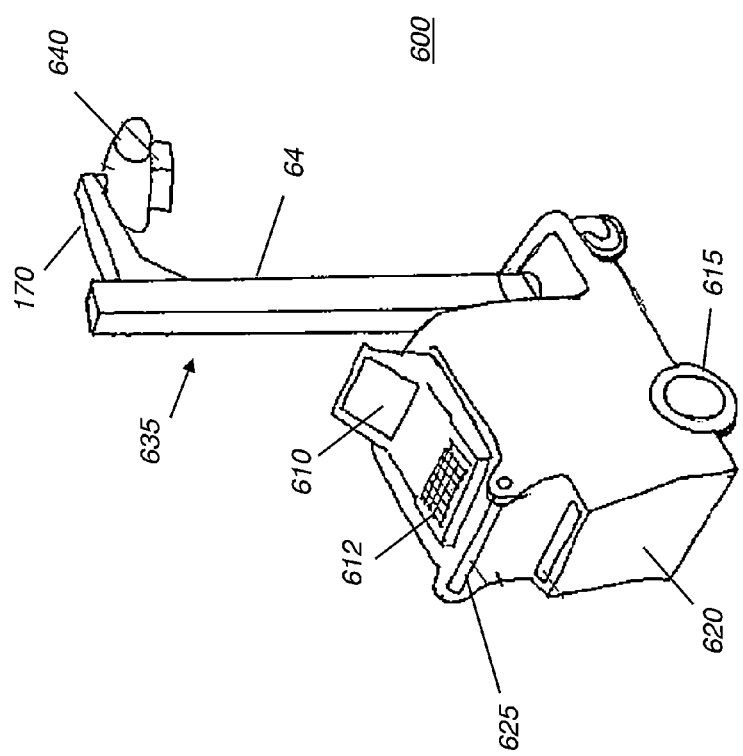
FIG. 1 shows a perspective view of one type of conventional mobile radiography unit.

The following is a description of exemplary embodiments of the invention, reference being made to the drawings in which the same reference numerals identify the same elements of structure in each of the several figures.

In the context of the present disclosure, the term "imaging receiver", or more simply "receiver", may include a cassette that has a photostimulable medium, such as a film or phosphor medium, for example, or may include a detector array that records an image according to radiation emitted from the radiation source.

As used herein, the term "energizable" indicates a device or set of components that perform an indicated function upon receiving power and, optionally, upon receiving an enabling signal.

Figure 2A:
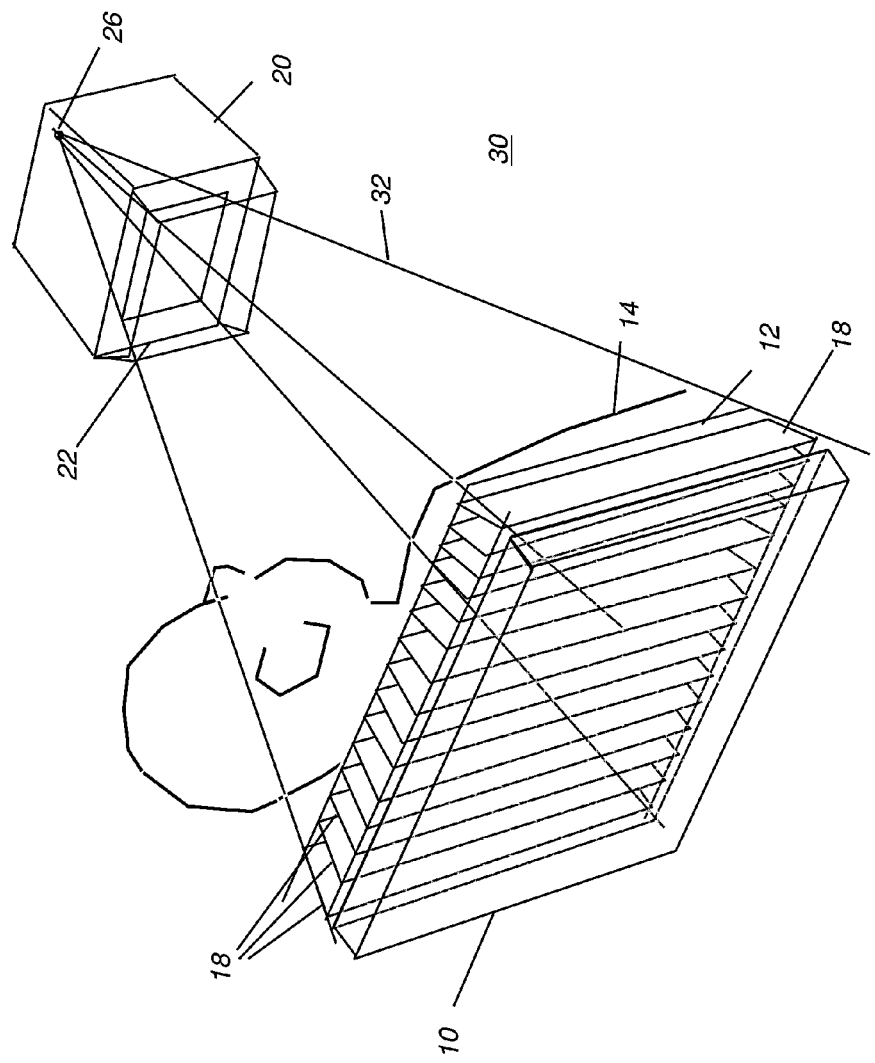
FIG. 2A is a perspective view showing the relative relationship of the patient being imaged to basic components of a diagnostic imaging apparatus.

The perspective schematic view of FIG. 2A shows components of a radiographic imaging apparatus 30 in which a radiation source 20 emits a radiation beam 32 that is shaped by a collimator 22 and directed toward a patient 14. A receiver 10 positioned behind patient 14 forms the diagnostic image from the incident radiation passing through the patient. Receiver 10 may have a photostimulable medium, such as a film or phosphor medium, for example, or may have a detector array that records an image according to radiation emitted from radiation source 20. Receiver 10 may have landscape or portrait orientation. An optional antiscatter grid 12 has plates 18 arranged as shown in FIG. 1, just above the surface of the receiver 10. Radiation source 20 acts as a point source 26. In addition to shaping radiation beam 32, radiation source 20 has an adjustable angular orientation for directing radiation toward receiver 10.

Figure 2B:
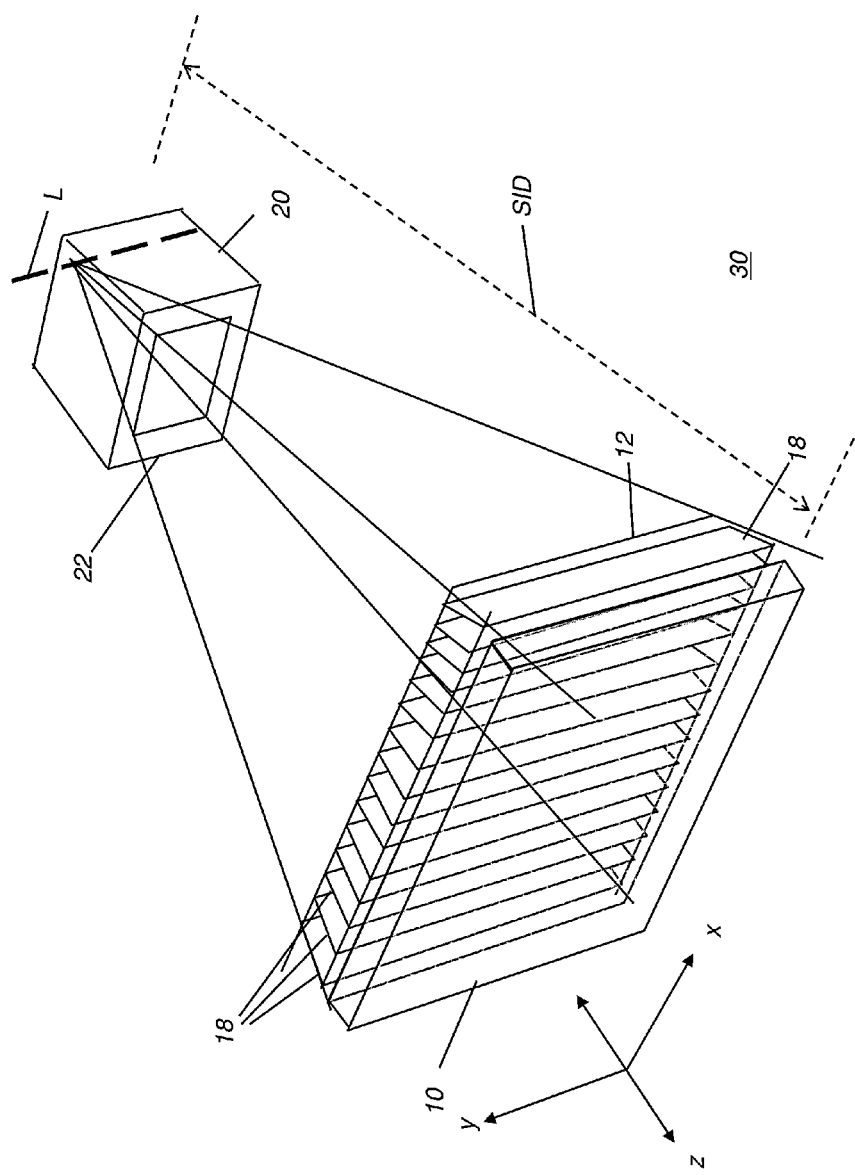
FIG. 2B is a perspective view showing a number of dimensional relationships for imaging system setup.

FIG. 2B (with patient 14 not shown for better visibility of system components) shows coordinate xyz axes. Here, the source-to-image distance (SID) is in the general direction of the z axis. In FIG. 2B, radiation source 20 is in its aligned position, at a suitable SID from receiver 10. Grid plates 18 are angularly arranged so that they define a focal line L where their respective planes converge at the SID. For best alignment for most imaging in such an embodiment, radiation source 20 should be centered near focal line L and have the face portion of collimator 22 generally parallel to the planar surface of receiver 10. However, there can be image types for which a slight angular offset is preferred.

Figure 2C:
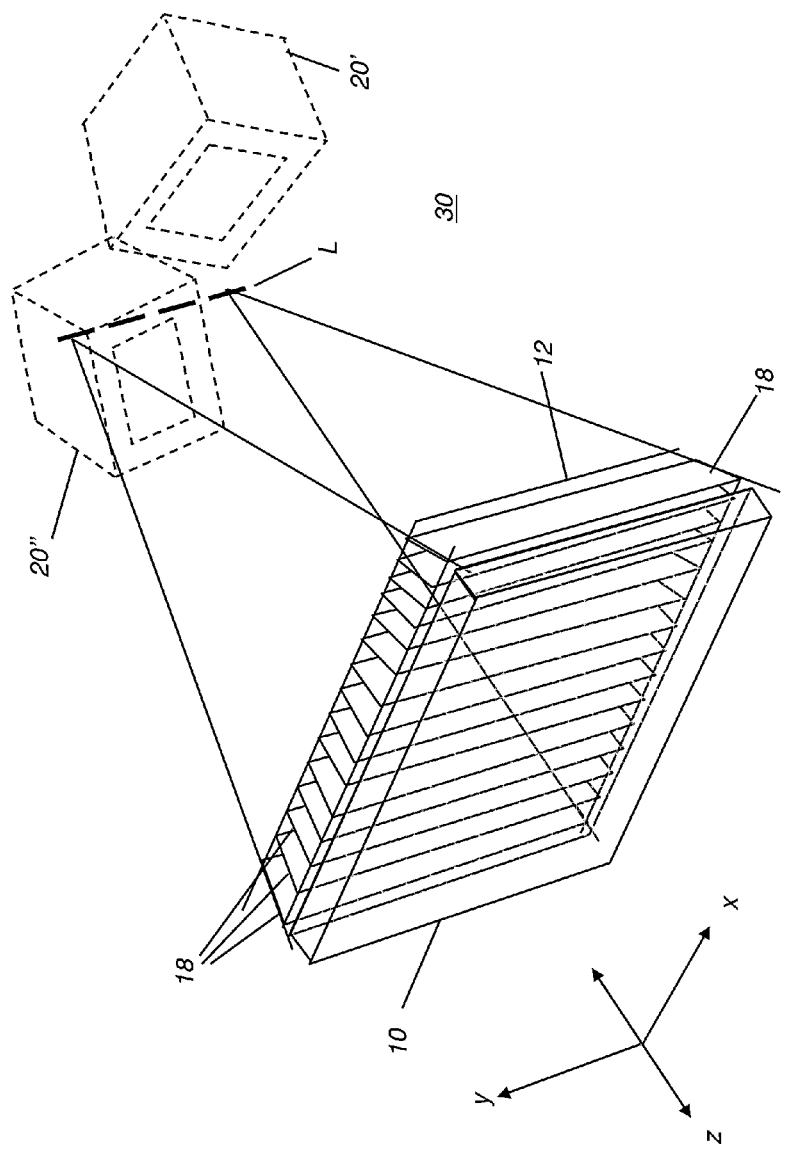
FIG. 2C is a perspective view showing exemplary out-of-alignment positioning.

FIG. 2C, by contrast, shows phantom outlines at 20' and 20" for poor positioning of radiation source 20. At positions 20' and 20" shown in phantom, the SID is almost acceptable; however, radiation source 20 is not centered near focal line L and its angular orientation is badly skewed. Alignment of the radiation source with the grid would be poor at these and similar out-of-alignment positions, degrading image quality or, at worst, preventing a suitable diagnostic image from being obtained.

Figure 3A:
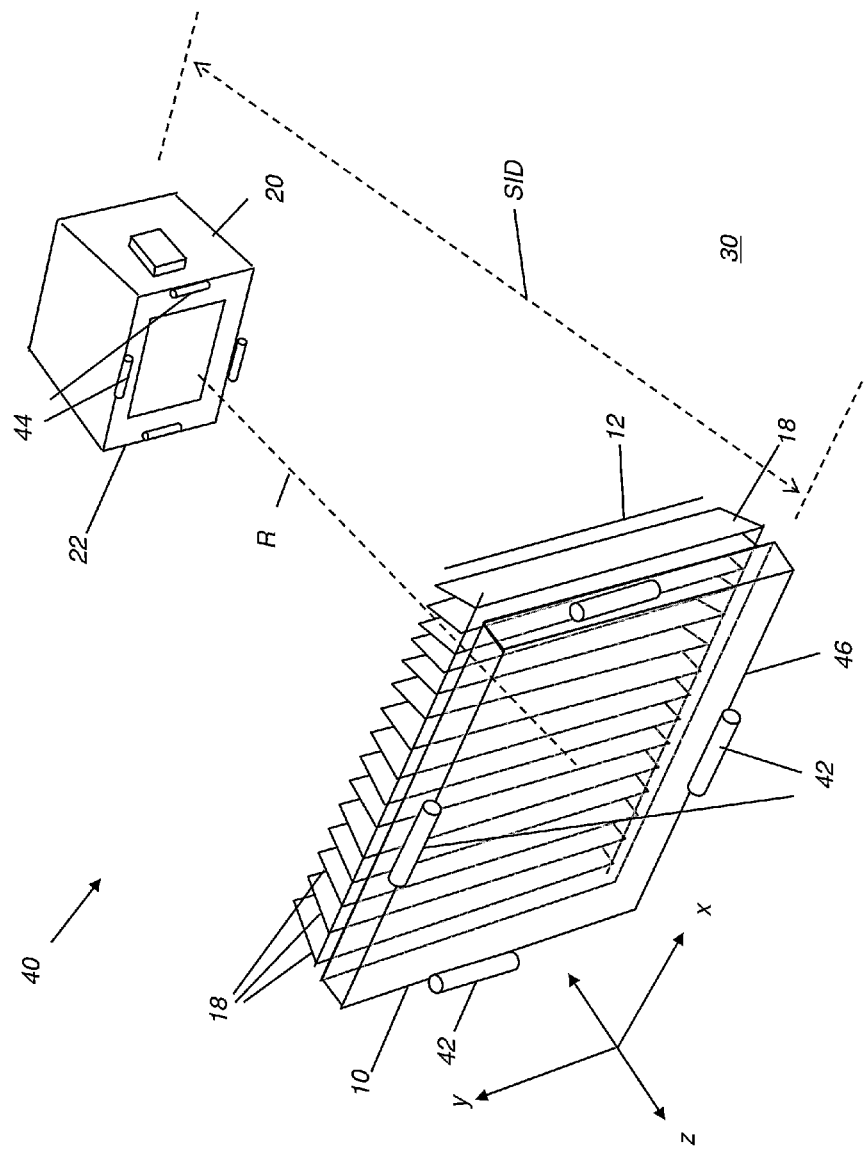
FIG. 3A is a perspective view showing the operation of one portion of an alignment apparatus in one embodiment.
Figure 3B:
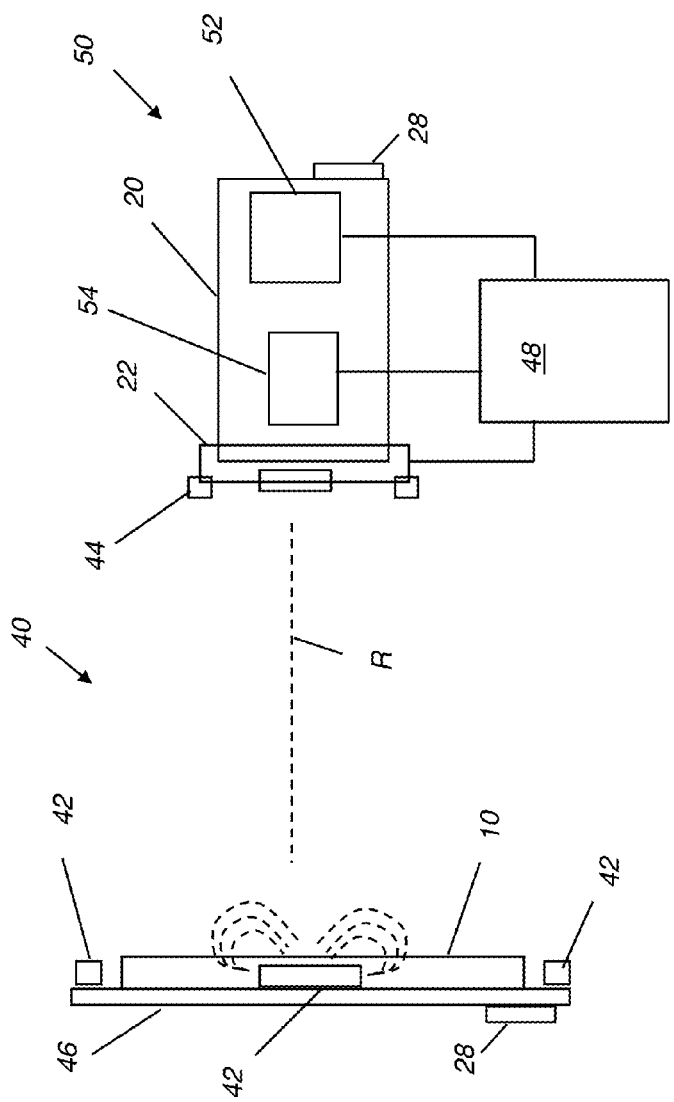
FIG. 3B is a side view block diagram that shows components used for achieving suitable tube to receiver/grid alignment according to an embodiment of the present invention.

The perspective view of FIG. 3A and side view of FIG. 3B show the use of a sensor apparatus 40 that is energizable to sense the relative spatial relationship between radiation source 20, having a radiation path represented as path R and distributed about a central axis, and imaging receiver 10 sensitive to radiant energy and positioned adjacent the subject for forming the radiographic image and to generate one or more output signals indicative of the relative spatial relationship. In the embodiment shown in FIGS. 3A and 3B, a holder 46 has one or more emitters 42 such as electromagnetic coils that generate an electromagnetic field or signal that is detected by one or more sensor elements 44, shown mounted near collimator 22. Holder 46 also holds receiver 10. In an alternate embodiment, sensor apparatus 40 components are built into receiver 10. In yet another alternate embodiment, signals are generated from one or more components on collimator 22 and detected by sensor elements on receiver 10. An additional inclinometer or other device for obtaining an angular measurement can optionally be provided on either or both receiver 10 or radiation source 20.

It can be appreciated by those skilled in the position-sensing arts that there are a number of possible configurations that can be used as sensor apparatus 40 for position sensing and for providing data for angle, SID, data for tracing the receiver 10 outline, and centering information where receiver 10 is positioned behind or underneath the patient. Centering relates to the position of the center of receiver 10 relative to the radiation path or, considered alternatively, the direction of the radiation path relative to the center of receiver 10. Source-to-object distance (SOD), here the distance between the x-ray source and the patient, can also be detected.

The position-sensing signal can be an analog signal or signals or one or more data values, for example. Signals can be from any of a number of types of sensor and sensor-reader apparatus, including inclinometers, radio-frequency devices, electromagnetic coils, and audio signals, for example. Sensors can be located in corners of the grid or the receiver, or may be integrated into the grid or receiver design itself. Whatever sensor configuration is used, the one or more position-sensing signals from sensor apparatus 40 go to a control logic processor 48 that provides the control logic for a display apparatus 50.

Display apparatus 50 is energizable to generate, in response to the position-sensing signals, a display that shows the technician the disposition of receiver 10 relative to radiation path R. In the embodiment shown in FIG. 3B, display apparatus 50 has both a display screen 52 that forms a displayed image to assist alignment and a projector 54 that forms a display by projection, wherein the projected display includes information to assist adjustment by projecting an image to indicate receiver location and related information. Display apparatus 50 may be equipped with either or both projector 54 and display screen 52 devices. In one embodiment, numeric SID and angular orientation values appear only on display screen 52, with centering data displayed using projector 54. Alternately, SID and angular orientation values can be projected onto the patient along with a centering target. It should be noted that display of the actual SID value can be particularly useful for radiographic imaging such as thoracic imaging, since there is an inverse squared relationship between the SID and the amount of radiation that is incident at the receiver. By way of comparison, the SID value is generally not a concern to the operator when obtaining dental and mammographic images, since close distances are used, with positioning and tolerances dictated by the design of existing radiological equipment and by conventional practices used for those types of imaging.

Figure 4:
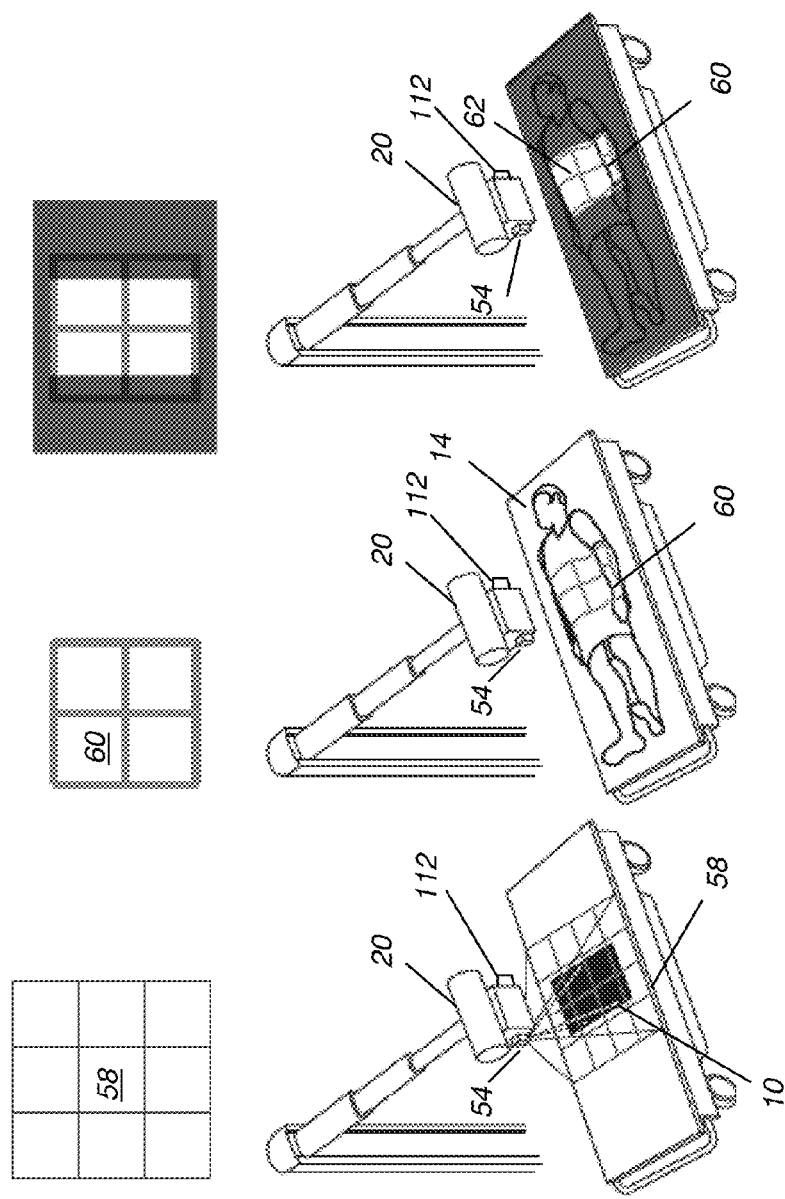
FIG. 4 shows perspective views of a projected image that is used to indicate the relative location of the receiver behind or underneath the patient.

The perspective views of FIG. 4 show how projector 54 performs the display function according to one embodiment of the present invention. Projector 54 can project light to form images over an image field 58 that exceeds the area of receiver 10, as shown at left. When receiver 10 is located using sensor apparatus 40, projector 54 displays a receiver pattern 60 on patient 14, wherein receiver pattern 60 indicates at least an outline showing the location of receiver 10 behind or underneath patient 14. At the right, the desired alignment is shown, wherein a collimator pattern 62, emitted from the collimator light source in the x-ray tube head, is aligned with receiver pattern 60. Notably, with this arrangement, projector 54 can project an image over an area that exceeds the size of receiver 10, enabling the outline of receiver 10 to be displayed prior to centering of the collimator and radiation path onto receiver 10. An optional autofocus apparatus 112 is also provided for reporting needed adjustments to focus for projector 54.

Figure 5:
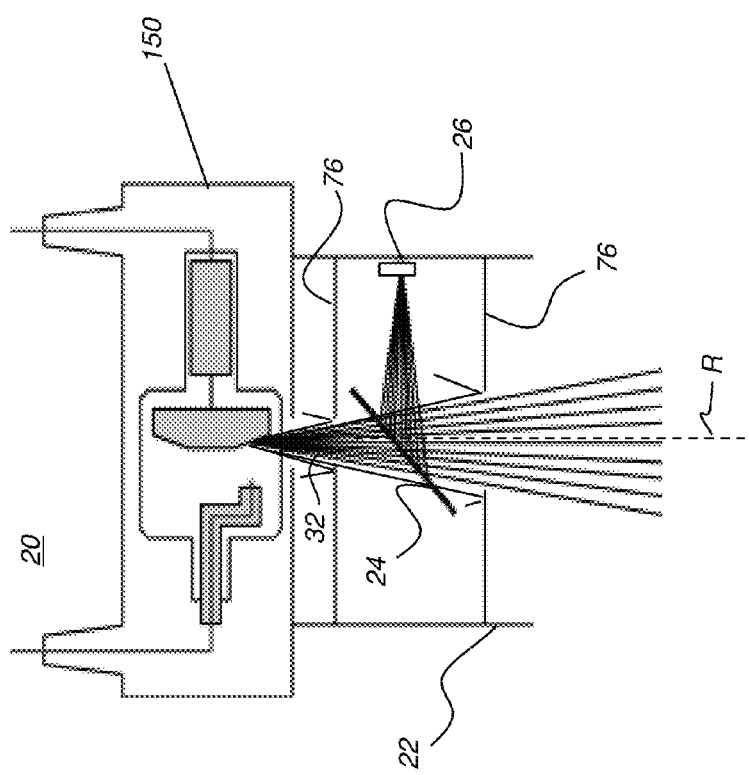
FIG. 5 is a schematic diagram of a conventional x-ray source and collimator light.

The cutaway cross-sectional view of FIG. 5 shows a conventional radiation source 20 in an enclosure 150, commonly termed an x-ray head, with a collimator light 26. Collimator light 26, typically a light bulb or light emitting diode (LED) or other solid-state light source, mounts inside collimator 22. A mirror 24, essentially transparent to x-rays, combines the light path of collimator light 26 with the radiation path R of x-ray beam 32, so that the cross-sectional area of the light beam from collimator light 26 matches the cross-sectional area of the radiation emitted from radiation source 20.

Figure 6A:
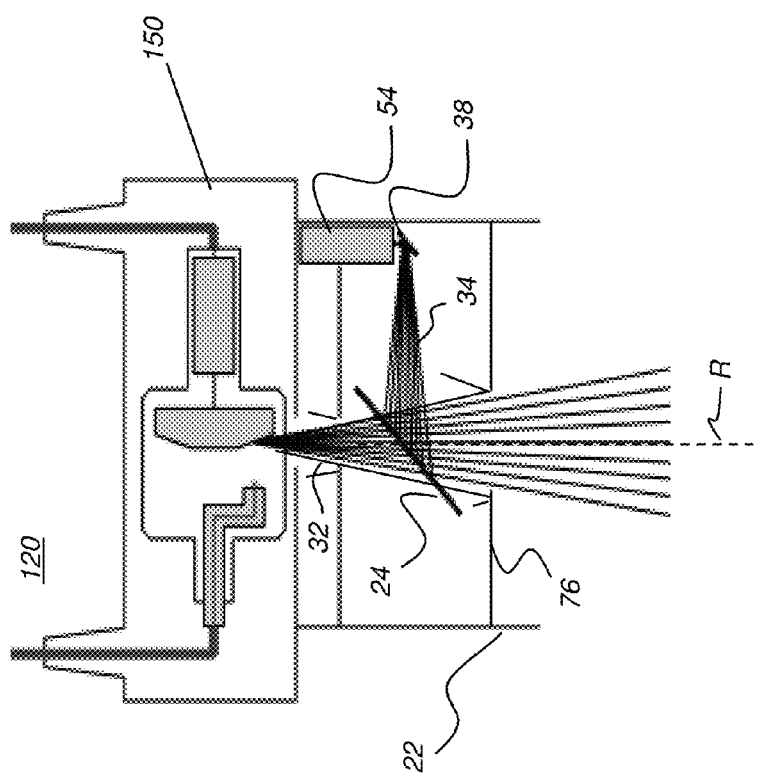
FIG. 6A is a schematic diagram that shows an embodiment of the present invention that replaces the conventional collimator light with a projector and uses a mirror for redirection of the projector output.
Figure 6B:
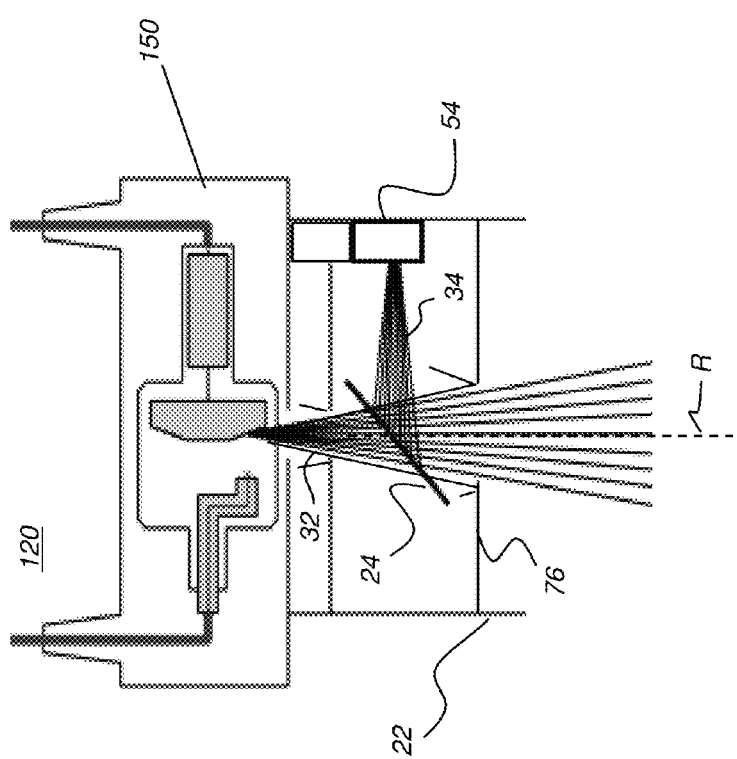
FIG. 6B is a schematic diagram that shows an embodiment of the present invention that replaces the conventional collimator light with a projector, without using a mirror for redirection.

The cutaway cross-sectional view of FIG. 6A shows an embodiment of a radiation source 120 that replaces collimator light 26 of FIG. 5 with digital projector 54 that is coupled to enclosure 150 and emits a projector light 34. In the FIG. 6A embodiment, a mirror 38 deflects projector light 34 toward combining mirror 24. The FIG. 6B embodiment is similar, but without the need for mirror 38. As can be seen by comparison with FIG. 5, beyond mirror 24, the path of projector light 34 is the same as the path of light from collimator light 26 in both FIG. 6A and 6B embodiments. The projector light is directed along radiation path R and with the beam shaped by collimator 22, through collimator blades 76. Advantageously, with the arrangement of FIGS. 6A and 6B, the beam diameters of the radiation beam and the collimator light are also identical for light beyond mirror 24. As shown in FIGS. 5, 6A, and 6B, collimator blades 76 shape the output beam and collimator light by blocking a portion of the emitted radiation or light. It should also be noted that some collimator arrangements use a single blade, rather than having multiple blades 76 as shown in FIGS. 5, 6A, and following.

Figure 7:
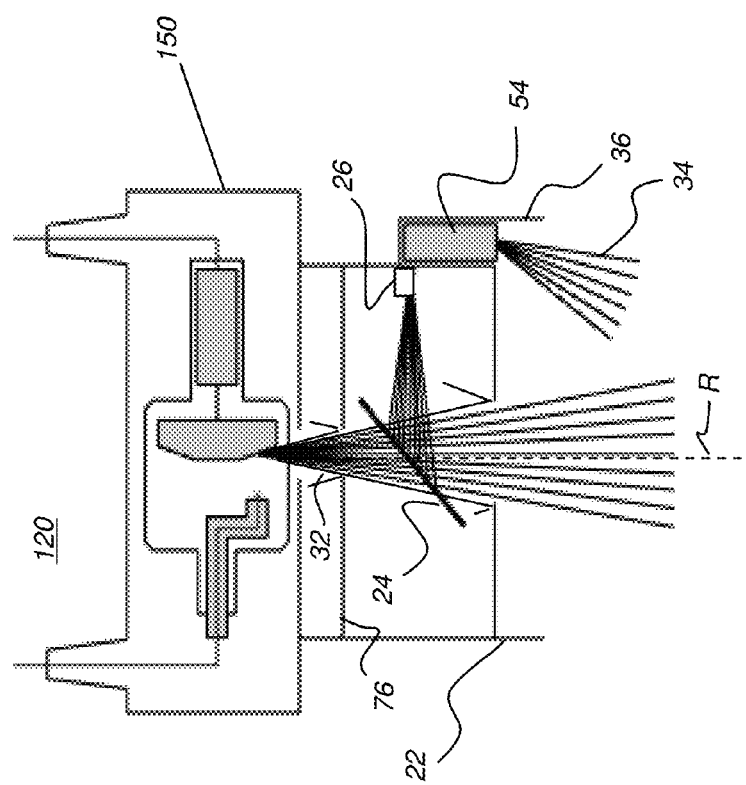
FIG. 7 is a schematic diagram that shows an alternate embodiment of the present invention in which the projector is added to an existing x-ray head.

The cutaway cross-sectional view of FIG. 7 shows an alternate embodiment of radiation source 120 in which projector 54 mounts in a housing 36 along the side of collimator 22 but does not replace collimator light 26. This alternate embodiment introduces possible parallax problems because the light path of projector light is spaced apart from radiation path R. These parallax problems can be corrected provided that the distance from radiation source 120 and the patient can be determined, as described in more detail subsequently.

Figure 8:
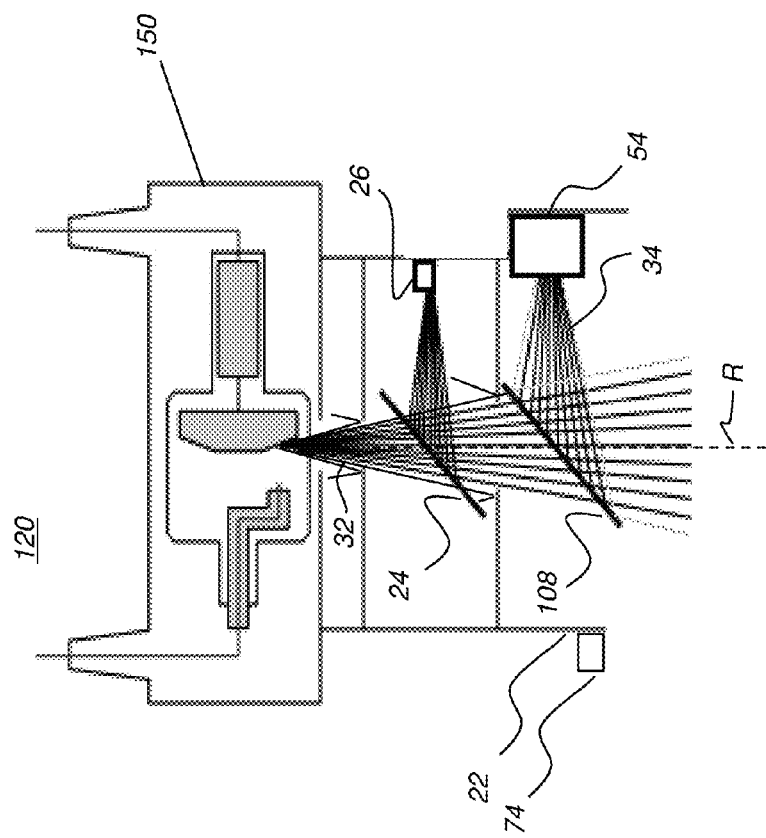
FIG. 8 is a schematic diagram that shows another alternate embodiment of the present invention in which the projector is added to an existing x-ray head.

The alternate arrangement of FIG. 8 uses a second mirror, two-way mirror 108, to align the path of projector light 34 with radiation path R, eliminating the parallax error condition. This arrangement allows projector 54 to project light over a broader angular range than with the FIG. 6A/6B arrangement. An optional sensor 74 provides positional information about the angular setting of collimator 22. Sensor 74 could be used with any of a number of embodiments of the present invention, but is particularly useful where projector 54 can form an image over a broader area than that defined by the collimator blades.

The schematic perspective view of FIG. 9 shows one advantage where projector 54 is mounted alongside radiation source 20. Here, projector 54 can project light to form images over an image field 58 that exceeds the area of a collimator pattern 62 that can be illuminated using the FIG. 6A or 6B embodiments.

Projector 54 can be any of a number of types of devices that are capable of providing a display onto the patient or other subject being imaged. In one embodiment of the present invention, projector 54 is a pico-projector, such as a Pico Projector Display from Microvision Inc., Redmond, Wash., USA, or a Micro Projector from AAXA Technologies, Inc., Santa Ana, Calif., for example. Image forming devices such as these are advantaged for a number of reasons, including small size, low weight, and low power requirements. These small-footprint projectors, currently used in cell-phone and other highly portable electronic devices, scan one or more low-power solid-state light sources, such as light-emitting diodes (LEDs) or lasers onto a display surface. This type of projector requires a small number of optical components for projection over a range of distances. The solid-state light source itself can typically be turned on and off rapidly as needed, to limit power consumption. This allows the display device to operate at low power levels, so that battery power could even be used for projector 54. Alternate embodiments use other types of electronic imaging projectors as image forming apparatus, such as those that employ, as spatial light modulators, a digital micromirror array such as the Digital Light Processor (DLP) from Texas Instruments, Inc.; an array of micro-electromechanical grating light valves, such as the Grating Light Valve (GLV) device from Silicon Light Machines, Inc.; or a liquid crystal device (LCD) including a Liquid Crystal on Silicon (LCOS) device.

Figure 10A:
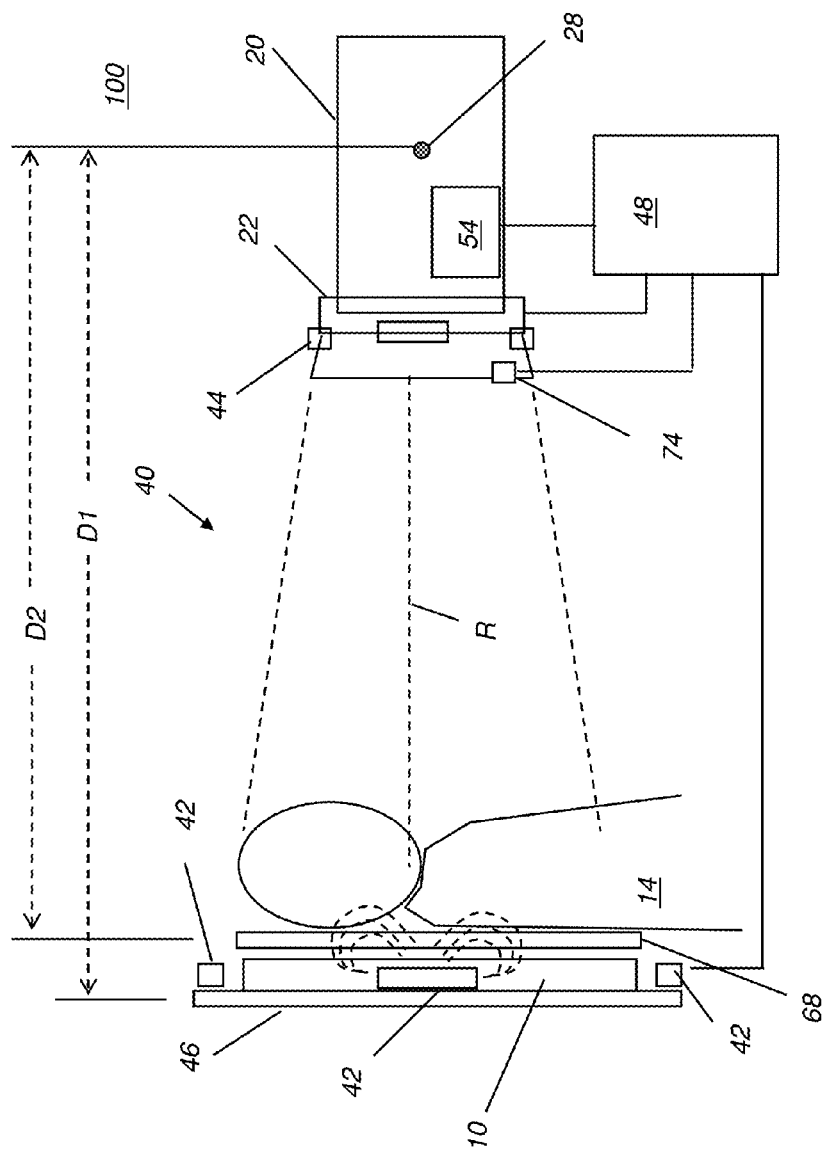
FIG. 10A is a schematic block diagram that shows components of an imaging apparatus that is configured to identify the position of the imaging detector.

One advantage of digital projector 54 is its ability to display any type of image that can be programmed and to change the displayed image dynamically as needed. The schematic side view of FIG. 10A shows components of a radiographic imaging apparatus 100 for obtaining x-ray images according to an alternate embodiment of the present invention in which various spatial and operational parameters can be determined by sensor apparatus 40 and used by the system. A combination of emitters 42 and sensor elements 44 determine distances D1 and, optionally D2, and orientation between receiver 10 and point source 28 within radiation source 20. In FIG. 10A, distance D1 is measured from receiver 10 to point source 28. Distance D2 is measured from an automatic exposure control (AEC) device 68 to point source 28. A control logic processor 48, such as a microprocessor, dedicated processor, or attached computer, obtains distance and spatial orientation values and controls projector 54 accordingly, so that suitable information can be projected onto patient 14 or other subject to be imaged. It can be appreciated that any number of possible arrangements of signal emitting and sensor elements can be used in an arrangement similar to that shown in FIG. 10A for determining parameters such as angular orientation, aim centering, source-to-image distance (SID), and other variables that are of interest for obtaining a suitable radiographic image, whether for a mobile or fixed-position radiography apparatus. Optional sensor 74 provides control logic processor 48 with feedback information on the settings of collimator 22. This information can be used to determine the boundary and outline of the radiation path as defined by collimator 22.

With respect to FIG. 10A, it can be appreciated by those skilled in the position-sensing arts that there are a number of possible configurations that can be used as sensor apparatus 40 for position sensing and for providing data for angle, SID, data for tracing the receiver 10 outline, and centering information where receiver 10 is positioned behind or underneath the patient. Centering relates to the position of the center of receiver 10 relative to the radiation path or, considered alternatively, the direction of the radiation path relative to the center of receiver 10. Source-to-object distance (SOD), here the distance between the x-ray source and the patient, can also be detected. A position-sensing signal can be an analog signal or signals or one or more data values, for example. Signals can be from any of a number of types of sensor and sensor-reader apparatus, including inclinometers, radio-frequency devices, electromagnetic coils, and audio signals, for example. Sensors can be located in corners of the grid or the receiver, or may be integrated into the grid or receiver design itself.

For FIGS. 7 and 8 embodiments in which projector 54 is coupled to enclosure 150 but does not replace collimator light 26, SOD distance information can be used to correct for parallax error, so that the projected collimator pattern 62 properly coincides with the outline of the collimated radiation beam 32.

Figure 10B:
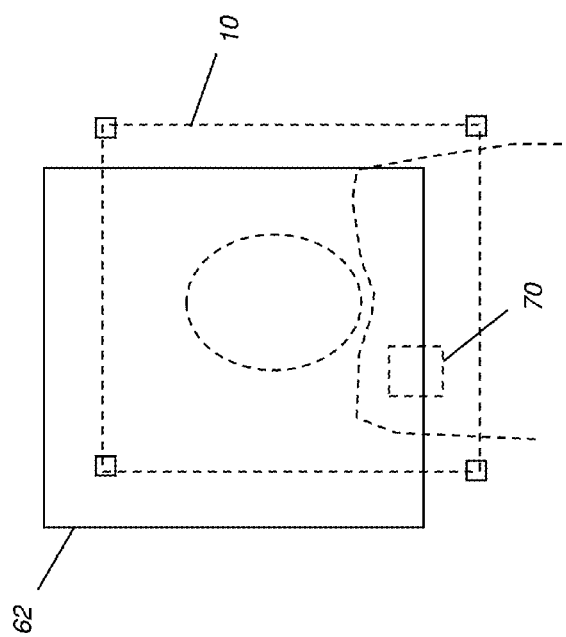
FIG. 10B is a schematic diagram that shows misalignment of the collimator to the detector.
Figure 10C:
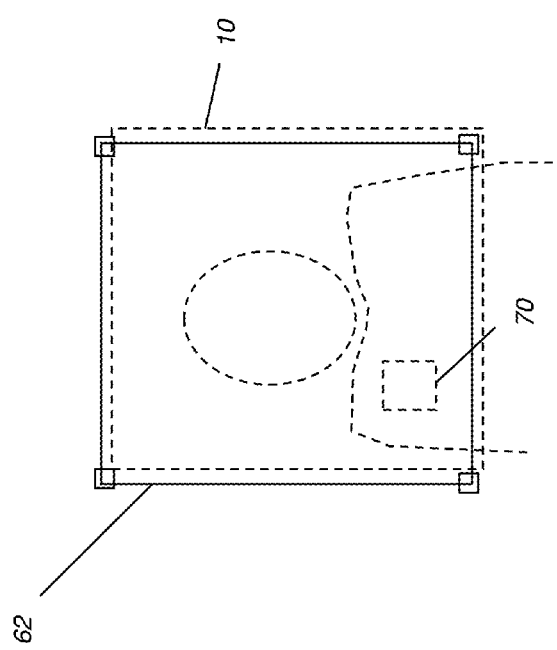
FIG. 10C is a schematic diagram that shows improved alignment of the collimator to the detector.

FIG. 10B shows one condition of interest to the technician for properly aiming and aligning the x-ray head and setting collimator blades, using feedback information from sensors as in the example of FIG. 10A. Here, the position of receiver 10 is shown in dashed outline; the position of collimator pattern 62 is offset from receiver 10. Also shown in dashed outline is the position of an AEC sensor 70. FIG. 10C shows a more desirable arrangement, in which the projected collimator pattern 62 is more generally centered on receiver 10. In a fixed-position system, this arrangement can be automatically obtained. In a mobile radiography system, the arrangement of FIG. 10B is more likely, but can be corrected using a sensing system such as that shown in FIG. 10A.

Figure 11A:
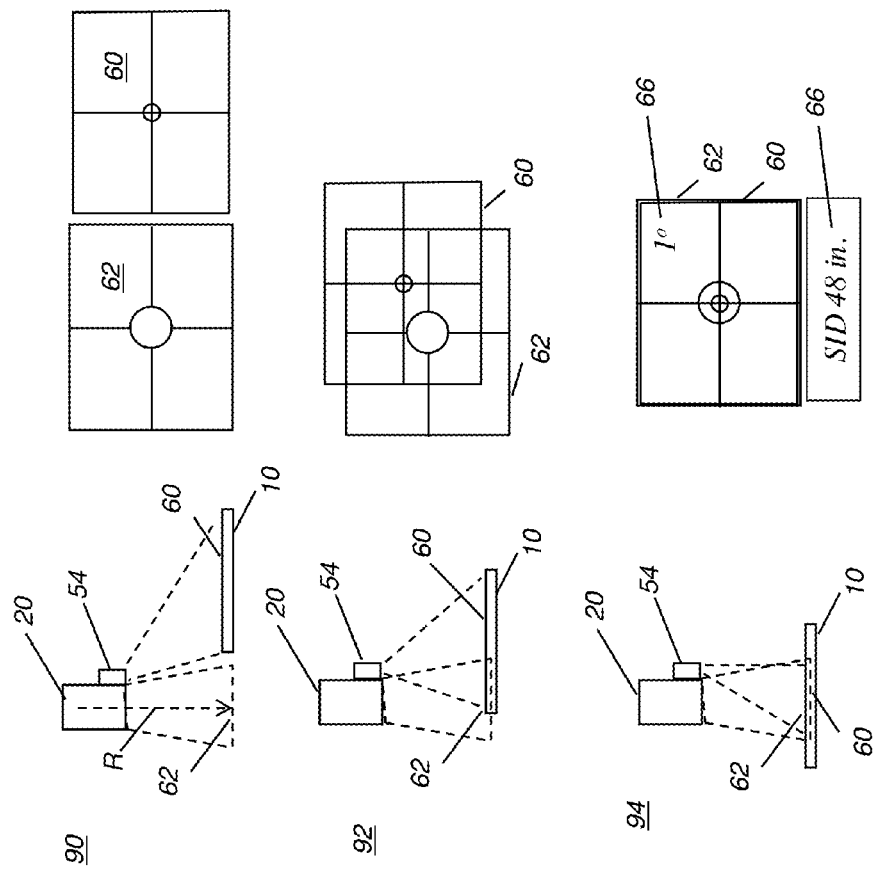
FIGS. 11A and 11B are diagrams that show how projected light patterns align under various conditions, including centering, angular, and distance differences.
Figure 11B:
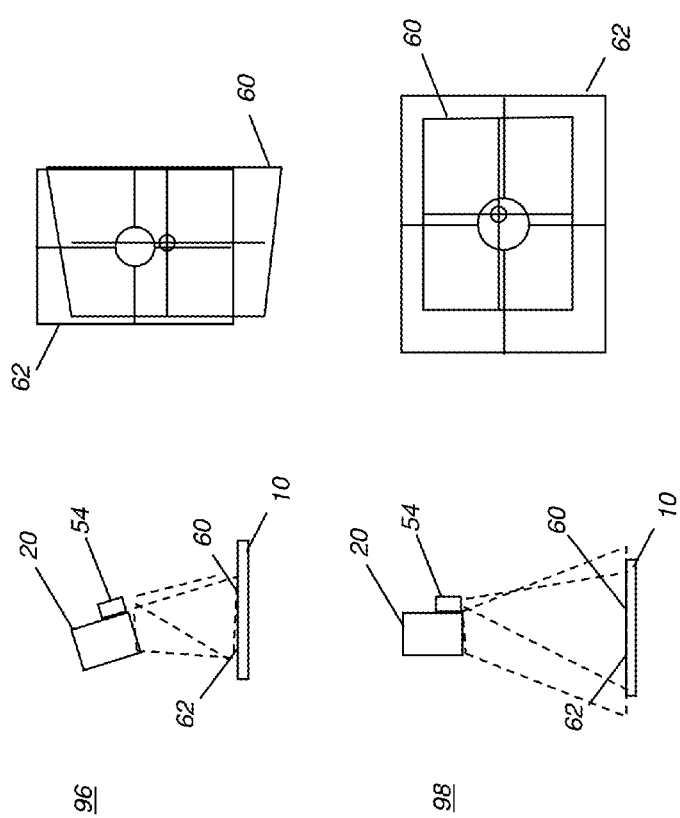

The positional relationship of displayed patterns from projector 54 and from the collimator light of the x-ray tube head can be used as indicators of alignment. By way of example, FIG. 11A shows how alignment of collimator pattern 62 from the collimator light with receiver pattern 60 from projector 54 indicates needed alignment adjustment of radiation source 20 with its receiver 10. The patterns shown at 60 and 62 are representative examples selected for illustration and can take any of a number of forms, including, but not limited to, crosshair patterns, including crosshair patterns with or without a central circle as shown in the example of FIGS. 11A and 11B. At a relative position 90, source 20 and receiver 10 are not aligned and respective patterns 62 and 60 indicate this misalignment. At a relative position 92, source 20 is closer to alignment with receiver 10, closer to centering than shown at position 90, and patterns 62 and 60 display as somewhat overlapping but are not centered with respect to each other. At a relative position 94, source 20 and receiver 10 are aligned and the displayed respective patterns 62 and 60 are overlaid to indicate this centering alignment. In addition, position 94, with both patterns 60 and 62 at the same size and over substantially the same area, also indicates that the collimator has been properly set to limit the radiation distribution and to reduce the likelihood of backscatter. Values 66 for SID and angle are also displayed by projector 54. In an alternate embodiment, a source-to-object distance (SOD) also displays. The projected values can be positioned within or outside receiver pattern 60. In alternate embodiments in which collimator blade position can be sensed, additional information on properly sizing and orienting the collimated light beam can also be provided in the display.

FIG. 11B shows other examples that represent poor relative positioning of source 20 and receiver 10. In a relative position 96, source 20 is nearly centered with respect to receiver 10, but the angle is skewed from normal. Receiver pattern 60 is accordingly non-rectangular, such as having a keystone pattern, for example, indicating the angular relationship of the radiation path from source 20 and receiver 10. In a relative position 98, source 20 is nearly centered with respect to receiver 10, but either the source-to-image distance (SID) is incorrect or, if correct, the collimator should be adjusted to reduce backscatter. In this case, the respective patterns 60 and 62 appear to be of different sizes to indicate the need for SID or collimator adjustment.

Where projection is used for display apparatus 50, in addition to the receiver 10 outline, information of various types can be displayed on or alongside the patient, for example:

a) Location of the receiver shown with a colored light. Using the same sensors that assist with alignment the apparatus can detect and highlight the outline of the imaging receiver.

b) AEC location shown relative to the patient. Different display representation is used for active and inactive AEC cells. Projection display of the AEC location is described in commonly assigned, copending U.S. patent application Ser. No. 13/083,776, filed Apr. 11, 2011.

c) Grid information, including grid ratio, transverse vs. longitudinal grid orientation.

d) The actual SID and the recommended SID displayed, either by default or provided by system logic, given the type of exam and grid used.

e) Information on Patient, Exam information: Patient Name, Room#, Patient ID, DOB, displayed to confirm that this is the correct patient and the correct exam.

f) A partial subset of the alignment information displayed on a display monitor, as described subsequently, projected onto the patient.

g) Recommendation for collimator blade settings, based on the image type that is to be obtained.

Figure 12A:
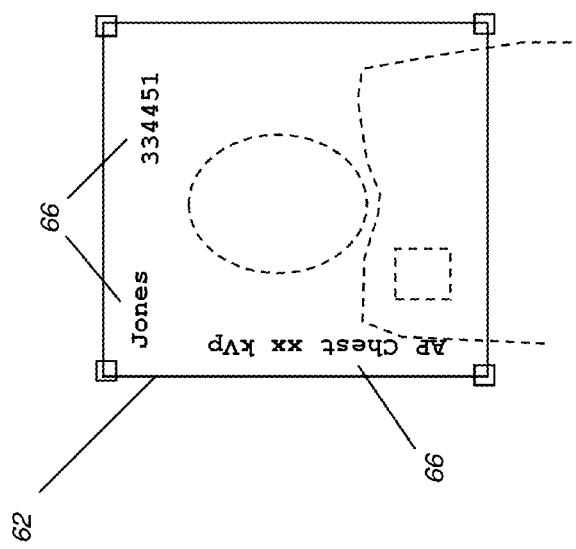
FIG. 12A is a plan view showing textual information displayed by a projector when used as collimator light.

FIGS. 12A, 12B, 12C, 12D, and 12E show various types of information and prompts that can be provided for providing instructions or guidance to the operator or for listing information about the patient that may be relevant for the imaging exam. FIG. 12A shows a number of text fields 66 that can be provided, such as for patient identification, to show exam type or variable settings, and other useful information. Because this data is displayed from projector 54, the information provided can be in any selected language or font or can be projected in any suitable color, including a color that is different from the outline that is provided as collimator pattern 62. Information can display momentarily, such as during initial setup, or be periodically displayed. Text fields can scroll across collimator pattern 62, such as along an edge of pattern 62.

Figure 12B:
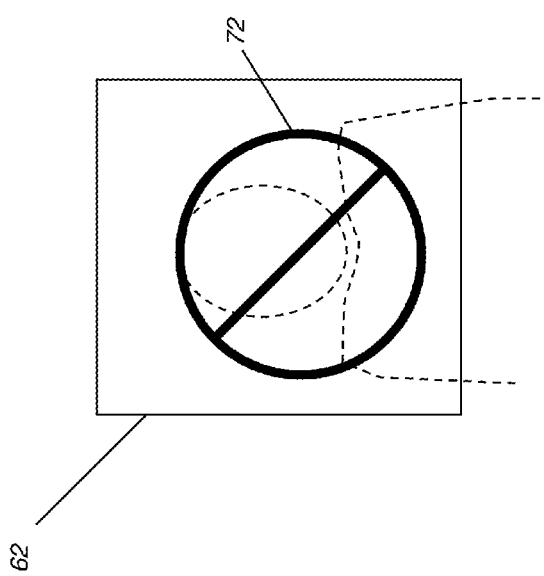
FIG. 12B is a plan view showing symbolic information displayed by a projector when used as collimator light.

FIG. 12B shows a symbol 72 that is displayed by projector 54 to help provide operator instructions, such as error information when sensed setup parameters are not compatible with the image type or other discrepancy is detected by control logic processor 48.

Figure 12D:
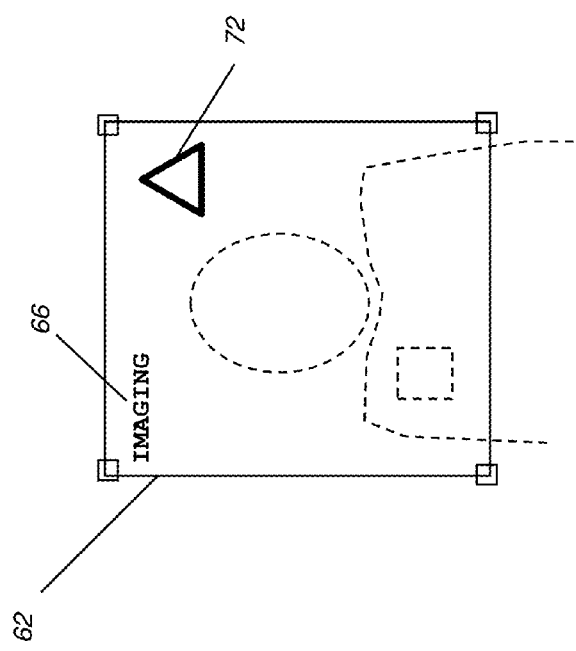
FIG. 12D is a plan view showing status information displayed by a projector when used as collimator light.

FIG. 12C shows a progression of collimator patterns 62, each separately numbered or otherwise labeled. This arrangement can be used, for example, for long-length imaging applications, in which the length of the subject that is to be imaged exceeds the corresponding dimensions of the imaging detector, so that the receiver 10 must be shifted in position and radiation source 20 redirected to obtain successive images that must then be stitched together. Text field 66 in FIG. 12D is a status message that may flash, move, or appear in a different color during different phases of setup or imaging. Symbol 72 can display according to imaging status. Animation using symbols 72 with associated text can also be projected to provide status, warning, or instructional information. Instructions may include recommendations for grid usage.

Useful instructional or error information that can be projected includes setup information that may also appear on a display screen. This can include reporting an error condition related to wall stand movement or other condition for which the technician may not be otherwise aware. Colors, patterns, animation, and other effects can be used to report status or error conditions or to instruct the technician to refer to a display monitor, for example, for information on system error or status.

In addition to the display of collimator-related information, projector 54 can also display information related to the relative position of receiver 10 and AEC sensor 70 where this information is available to control logic processor 48. Thus, for example, the misalignment shown in FIG. 10B could be represented by outlines projected for the collimated beam as collimator pattern 62 as well as outlines for receiver 10 and AEC sensor 70, such as in different colors. Referring to FIG. 9, field 58 for projection extends beyond the confines of the collimated beam in embodiments shown in FIGS. 7 and 8 in which projector 54 is provided in addition to collimator light 26. Thus, for embodiments using either of these arrangements, outline projection for misalignment as well as textual or symbolic information can be provided outside the boundary of collimator pattern 62. Collimator pattern 62 can be any suitable pattern for outlining the boundary or indicating the center of the radiation path.

Projector 54 focus can be achieved in a number of ways. Laser projectors do not need focus adjustment. Autofocus apparatus can be used for other projector types, using a range-finding signal such as an ultrasonic signal or infrared (IR) light, for example, to measure the distance from the source to the subject being imaged. Autofocus and range-finding methods and devices are inexpensive and well-known to those skilled in the image capture arts. Alternately, information from sensor apparatus 40 can be used to determine the focus distance and used for automatic focusing. Focus can also be approximated, such as by using standard source-to-object distances, for example.

Using an arrangement of sensing and detection components such as that shown by way of example in FIG. 10A, projector 54 can provide not only a collimator light, but also an indication of relative location for AEC sensors and the receiver itself. This can be of particular value for a mobile radiographic apparatus, in which the relative positions of radiation source and detector are not fixed and where there can be some variation in beam centering and other alignment. Thus, for example, projector 54 can, at the same time, show the detector 10 outline, the collimator outline, and the location of an AEC sensor, all projected onto the patient. Both existing and desired locations can be displayed.

Figure 12E:
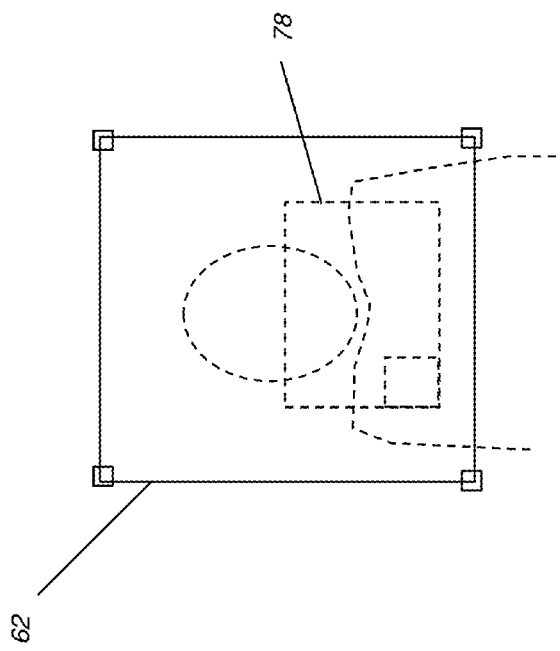
FIG. 12E is a plan view showing an outline that is displayed by a projector used as a collimator light.

In one embodiment, as shown in FIG. 12E, projector 54 is used to project an outline 78 that has a predetermined shape or predetermined dimensions that are smaller than the detector, such as a standard cassette size or "virtual" cassette size, for example. Alternately, a standard image size can be represented, projected onto the patient. This represents a cropped image size for a DR panel. The operator can then use this projected outline as a guide for setting the collimator and for adjusting the head angle.

The invention has been described in detail with particular reference to a presently preferred embodiment, but it will be understood that variations and modifications can be effected within the spirit and scope of the invention. For example, audible feedback tones could be used to supplement display functions for obtaining the needed adjustments for alignment. A digitally controlled collimator can provide dimensional information about collimator settings that can be useful for projecting information on the size and centering of the image to be obtained and other data. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A radiography system for obtaining a radiographic image of a subject, the system comprising:
a radiation source within an enclosure, the radiation source energizable to direct radiant energy along a radiation path toward an imaging detector, where the radiation path is defined according to a collimator; and
a digital projector that is coupled to the enclosure and is energizable to provide an illumination beam that outlines the defined radiation path, where the digital projector comprises a light modulator including a digital micromirror device, an array of micro-electromechanical grating light valves, and a liquid crystal device, where the digital projector comprises a solid-state light source, or where the digital projector is a color projector.

2. The radiography system of claim 1 further comprising a beam combiner that is in the path of both the directed radiation source and the digital projector and a collimator light disposed within the enclosure.

3. The radiography system of claim 2 where the illumination beam of the digital projector and an illumination beam of the collimator light are both aligned to the radiation path of the radiation source.

4. The radiography system of claim 1 further comprising a sensor apparatus that is energizable to detect the spatial position of the imaging detector, or energizable to detect the spatial position of an automatic exposure control sensor.

5. The radiography system of claim 1 where the digital projector is energizable to display a collimator pattern that shows the radiation path and to display additional information along an area lying outside of the displayed collimator pattern.

6. The radiography system of claim 1 where the digital projector is mounted inside the enclosure in front of the radiation source, outside the enclosure or inside the enclosure in front of the collimator.

7. The radiography system of claim 1 where the digital projector is configured to display a selected radiation path, a current radiation path and corrective actions responsive to at least an angle of the detector, center position of the detector and distance to the detector to move the current radiation path toward the selected radiation path.

8. A method for obtaining a radiographic image of a subject, the method comprising:
defining a radiation path for energy from a radiation source that is mounted within an enclosure, where the radiation source is energizable to direct radiant energy along a radiation path toward an imaging receiver, where the radiation path is defined according to an adjustable collimator; and
coupling a digital projector to the enclosure, the digital projector is energizable to direct visible light along the defined radiation path in accordance with the collimator adjustment; and
energizing the digital projector and displaying at least information related to the radiographic image to be obtained, where the displaying the information related to the radiographic image comprises displaying projected text or symbols.

9. The method of claim 8 further comprising displaying at least the outline of the radiation path.

10. The method of claim 8 where the projected text moves relative to the displayed outline.

11. The method of claim 8 where the displaying the information related to the radiographic image comprises displaying using different colors, where the displayed text or symbols are in a different color from the displayed outline.

12. The method of claim 8, where the displaying the information related to the radiographic image comprises displaying an outline of the imaging receiver, where the imaging receiver is not mechanically connected to the radiation source.

13. The method of claim 8, where the displaying the information related to the radiographic image comprises displaying status information about the image to be obtained, further comprising providing a status message before the radiant energy is directed to the imaging receiver.

14. The method of claim 8, where the displaying the information related to the radiographic image comprises displaying (i) at least the outline of a desired radiation path and a current radiation path overlaid to indicate a relative spatial alignment therebetween and (ii) corrective action responsive to at least an angle of the imaging receiver, center position of the imaging receiver and distance to the imaging receiver.

15. The method of claim 8, further comprising displaying a sequence with a plurality of receiver outlines for successive images, where an actual position of the imaging receiver is not known relative to an actual position of the radiation source.

16. A mobile radiography apparatus comprising:
a moveable transport frame;
an adjustable support structure coupled to the moveable transport frame;
a radiation source within an enclosure, the enclosure coupled to the adjustable support structure, the radiation source energizable to direct radiant energy along a radiation path toward an imaging receiver, where the radiation path is defined according to a collimator;
a digital projector that is coupled to the enclosure and is energizable to provide an illumination beam that outlines the defined radiation path; and
a logic processor that is energizable to control emissions by the digital projector, where the where the illumination beam of the digital projector is aligned to the radiation path of the radiation source, where the digital projector is configured to display a selected radiation path, a current radiation path and corrective actions responsive to at least an angle of the imaging receiver, center position of the imaging receiver and distance to the imaging receiver to move the current radiation path toward the selected radiation path.

17. The radiography system of claim 16, where the digital projector comprises a light modulator including a digital micromirror device, an array of micro-electromechanical grating light valves, and a liquid crystal device, where the digital projector comprises a solid-state light source, or where the digital projector is a color projector.

18. The mobile radiography apparatus of claim 16, where the mobile radiography apparatus is a type configured to include a collimator light disposed within the enclosure to illuminate the current radiation path, where the digital projector replaces the collimator light disposed within the enclosure.

19. A radiography system for obtaining a radiographic image of a subject, the system comprising:
- a radiation source within an enclosure, the radiation source energizable to direct radiant energy along a radiation path toward an imaging receiver, where the radiation path is defined according to a collimator; and
- a digital projector that is coupled to the enclosure and is energizable to provide an illumination beam that outlines the defined radiation path,
- where the digital projector is energizable to display a collimator pattern that shows the radiation path and to display additional information along an area lying outside of the displayed collimator pattern.

20. A method for obtaining a radiographic image of a subject, the method comprising:
- defining a radiation path for energy from a radiation source that is mounted within an enclosure, where the radiation source is energizable to direct radiant energy along a radiation path toward an imaging receiver, where the radiation path is defined according to an adjustable collimator;
- coupling a digital projector to the enclosure, where the digital projector is energizable to direct visible light along the defined radiation path in accordance with the collimator adjustment; and
- energizing the digital projector and displaying status information about the image to be obtained, further comprising providing a status message before the radiant energy is directed to the imaging receiver.

21. A method for obtaining a radiographic image of a subject, the method comprising:
- defining a radiation path for energy from a radiation source that is mounted within an enclosure, where the radiation source is energizable to direct radiant energy along a radiation path toward an imaging receiver, where the radiation path is defined according to an adjustable collimator;
- coupling a digital projector to the enclosure, where the digital projector is energizable to direct visible light along the defined radiation path in accordance with the collimator adjustment; and
- energizing the digital projector and displaying (i) at least the outline of a desired radiation path and a current radiation path therewith to indicate a relative spatial alignment therebetween and (ii) corrective action responsive to at least an angle of the imaging receiver, center position of the imaging receiver and distance to the imaging receiver.

* * * * *